United States Patent [19]

Narasimhan et al.

Best Available Copy

[11] E Re. 30,753

[45] Reissued Sep. 29, 1981

[54] PROCESS FOR THE LARGE SCALE PRODUCTION OF HUMAN GROWTH HORMONE BY SERIAL SECONDARY SUSPENSION CULTURE

[75] Inventors: Mandayam J. Narasimhan, Bangalore, India; John A. Anderson, Menlo Park, Calif.

[73] Assignee: The Regents of the University of Minnesota, Minneapolis, Minn.

[21] Appl. No.: 109,908

[22] Filed: Jan. 7, 1980

Related U.S. Patent Documents

Reissue of:

[64] Patent No.: 4,124,448
Issued: Nov. 7, 1978
Appl. No.: 675,643
Filed: Apr. 9, 1976

[51] Int. Cl.[3] ..... C12P 21/00; C12N 5/02

[52] U.S. Cl. ..... 435/68; 435/241

[58] Field of Search ..... 435/68, 241

[56] References Cited

U.S. PATENT DOCUMENTS 3,073,746 1/1963 Thompson et al. ..... 435/241

OTHER PUBLICATIONS

The Merck Index–Ninth Edition, (1976), p. 7290.

Betteridge et al.–Chem. Abst., vol. 80, (1974), p. 44148k.

*Primary Examiner*—Sam Rosen

*Attorney, Agent, or Firm*—Burd, Bartz & Gutenkauf

[57] ABSTRACT

A new system of serially culturing human anterior pituitary gland cells in a new nutrient medium to produce large amounts of human growth hormone. Since only human growth hormone can be used to treat growth deficiencies in man, there is a great demand for the hormone, which is in relative short supply since only 2 to 3 mgs. of the human growth hormone can be extracted from one human pituitary gland obtained at autopsy. Using the new system of culture and new nutrient media, the human pituitary cells can be grown in vitro to produce in approximately three weeks, more than 20 times the amount of extractable growth hormone than that which was originally present in the original tissue now used for extracting the 2 to 3 mgs. of the hormone.

13 Claims, No Drawings

PROCESS FOR THE LARGE SCALE PRODUCTION OF HUMAN GROWTH HORMONE BY SERIAL SECONDARY SUSPENSION CULTURE

Matter enclosed in heavy brackets [ ] appears in the original patent but forms no part of this reissue specification; matter printed in italics indicates the additions made by reissue.

BACKGROUND OF THE INVENTION

This invention pertains to the field of medicine and medical biology. The specific sub-area of medicine and medical biology is the art of the in vitro culture of mammalian tissue cells. Many nutrient culture mediums have been developed and are, to a large extent, specifically designed to permit prolonged and sustained growth of specific types of cells, such as those derived from skin, from tumors, and from various other tissues in mammalian species. These are grown by primary culture systems as explants, monolayers or suspension cultures or secondary cell lines. However, there is no culture system or nutrient media available at the present which will permit prolonged growth and proliferation of human anterior pituitary growth hormone producing cells in sufficient number to provide a source of large amounts of growth hormone. This lack of success is related to many factors, among which are (1) limited knowledge concerning the specific nutrients for the specific cells, (2) the general trend for the pituitary growth hormone-producing cells to lose their function of producing growth hormone, (3) death of cells after a few days to a few weeks, and (4) transformation of cells to non-functioning fibroblastic or fibroblastoid type cells.

Some of the previous studies which indicate the difficulties encountered are as follows: Animal and human pituitary cells have been maintained as explants in cultures and are known to release their hormones for variable periods of time. Continuous cell lines derived from induced tumors in rats may proliferate for several weeks or a few months and are able to secrete some amounts of rat growth hormone. (Takemoto, H., Yokoro, K., Furth, J. and Cohen, A. I., Cancer Res., 22:917-924, 1962; Tashjian, A. H. and Hoyt, R. F., Jr., In Molecular Genetics and Developmental Biology, edited by M. Sussman, pp. 353-387, Prentice-Hall, New Jersey, 1972). Tumors of the human pituitary gland have also been maintained in culture and may secrete human growth hormone into the culture media for variable periods of time (Kohler, P. O., Bridson, W. E., Rayford, P. L. and Kohler, S. E., Metabolism, 18:782, 1969; Batzdorf, U., Gold, V., Matthews, N. and Brown, J., Neurosurgery 34:741, 1971; Peillon, F., Gourmelen, M., Donnadieu, M., Brandi, A., Sevaux, D. and Pham Huu Trung, M. T., Acta Endocrinol., 79:217-229, 1975) whereas normal human pituitary cells in culture survive and produce hormone only for a relatively brief period of time. The number of cells and the amount of hormone produced in such systems decline rapidly with time (Vidal-Tixier, A., Gourdji, D. and Tougard, C., Intern. Rev. Cytol., 41:173-239, 1975). Human fetal pituitary cells secreting growth hormone have also been cultured for several days but ultimately die or are transformed into fibroblast type cells (Gailani, S. D., Nussbaum, A., McDougall, W. J. and McLimans, W. F., Proc. Soc. Exp. Biol. and Med., 134:27-32, 1970).

The above described previously reported results by others were obtained by a culture procedure in which either small explanted pieces of tissue or a monolayer of cells were grown in small volumes in medium (Peillon et al, Vidal-Tixier et al and Gailani et al, cited above), into which only a small amount of growth hormone was released or secreted by the cells. The nutrient mediums used in these cultures have been unable to permit replication of the growth hormone producing cells. In all of these previously reported studies, the rate of cell multiplication and the amount of hormone produced, while persisting for a brief period of time, rather rapidly declines (Peillon et al). The culture systems or media used did not adequately meet the growth and metabolic needs of the cells as conversion to fibroblastoid cells, which are nonhormone producing or a loss of the growth hormone synthesis capacity in the cells or death of the cells occurred.

The literature concerning the art of tissue culture procedure and of nutrient medium developed is very voluminous and particularly extensive over the last 20 to 25 years. The inventors have, to date, been unable to find evidence of a previously described culture system or nutrient medium which permits the growth and proliferation of human growth hormone producing cells in sufficient amounts and over a long period of time to produce an adequate amount of growth hormone which can be biochemically extracted and used to treat growth hormone deficient states in man.

SUMMARY OF THE INVENTION

Broadly stated, the invention comprises a process involving a new culture system and new culture media for growing in vitro normal human pituitary cells for producing large amounts of human growth hormone. More specifically, the invention comprises a process for producing human growth hormone in which cells of the human anterior pituitary gland are dispersed in an amino acid-rich nutrient medium supplemented with liver extract, insulin and anti-biotic and anti-fungal agents and incubated under open-aeration cell growth conditions. The resulting culture is serially sub-cultured several times until the optimum desired cell growth level is achieved. The human growth hormone is extracted [from the cells] using conventional techniques.

DETAILED DESCRIPTION OF THE INVENTION

An exemplary nutrient medium rich in amino acids is that known as Medium 199-1X with Earle's modified salts (Proc. Soc. Exp. Biol. Med., 73:1, 1950, Growth, 15:11, 1951, Proc. Soc. Exp. Biol. Med., 74:22, 1950; Proc. Soc. Exp. Biol. Med., 78:880, 1951; J. Cell & Comp. Physiol., 36:411, 1950; J. Am. Med. Assn., 151:1081, 1953). To each liter of medium there is added from about 5 to 20 ml of liver extract, preferably about 10 ml; about 6 to 20 International Units of insulin, preferably about 10 I.U.; and minor amounts of anti-biotic and anti-fungal agents.

A preferred nutrient composition according to the present invention is as follows:

(1) Medium 199-1X with Earle's Modified Salts, GIBCO (Grand Island Biological Company), 1000 ml.

(2) Liver extract containing B vitamins (Lexavite Injectable, Eli Lilly and Company), 10 ml.

(3) Insulin, Crystalline, 10 International Units.

(4) Crystalline Sodium Penicillin G, 500,000 units.

(5) Streptomycin Sulfate, 500 mg.

(6) Nystatin, a polyene anti-fungal anti-biotic, 50,000 units.

The insulin should not be added to the medium until time of use because insulin will degrade in the medium between 4 and 8 days, particularly when kept at room temperature or above.

To achieve sustained growth and proliferation of human anterior pituitary cells and obtain a large cell mass to extract large amounts of human growth hormone, a novel modified system of culturing is used. This involves the growing of dispersed cells of the human anterior pituitary in containers containing our new medium with an open-aeration system for a period of several days, preferably about 8 days, followed by serial sub-culturing about every 4 to 8 days. The cultures may be grown as still-suspension cultures or as rotary suspension cultures. The technique involves greater degrees of aeration than is presently employed in culturing of human and mammalian cells. This is achieved by having open air vent caps on the containers which are placed in a 37° C. incubator with water troughs for moisture, provided with an airflow system of about 8 to 16 liters of sterile air per minute. Addition of 5% $CO_2$ to the air-flow which is usually employed in presently available tissue culture techniques is avoided since we have found that human pituitary cells do not grow well in the presence of 5% $CO_2$.

Following about 8 days growth the cultures are sub-cultured serially, utilizing an appropriate dilution range of 1 volume of medium containing cells added to 1 volume of fresh medium. The original culture may be divided into 2, 3 or more parts, depending upon the quantitative cell count found at each sub-culture time. If cell numbers are large by microscopic examination, greater sub-culture, dilution transfers should be employed. If cells are fewer in number, less dilution transfers of medium containing cells to fresh medium should be used. Cultures should be protected from bacterial, fungal and viral contamination at all times.

The invention is further illustrated by the following example: Using the preferred nutrient composition described above, an initial tissue inoculum (about $\frac{1}{3}$ of an anterior pituitary gland) was grown in serial culture with $\frac{1}{2}$ volume transfers every 8 days for 32 days. The following average concentrations of hGH in ng/ml found in the medium were: at 8 days 21,166; at 16 days 18,666; at 24 days 21,750; and at 32 days 20,000. Each culture flask contained 30 ml and hence because of one-half dilutions and volume reconstitution at sub-culture times, the total amount of hGH produced at each sub-culture time was as follows: 8 days 5.01 mg in 6 flasks; at 16 days 6.7 mg in 12 flasks; at 24 days 15.6 mg in 24 flasks; and, by 32 days 28 mg in 48 flasks. Cultures have been grown for as long as two months. Preliminary characterization studies utilizing a Sephadex gel filtration procedure indicate that 80 to 90% of the immune reacting hGH is a monomer. Cells were epithelial type, 10–14$\mu$ in diameter, contained chromatin granules and a large highly chromatic nucleus. Mitosis was present.

By this new technique of serial sub-culture, one is able to obtain a large mass of human pituitary cells for producing large amounts of human growth hormone, in relatively short periods of time.

The effectiveness of the medium resides in the addition of certain of the medium components which have not heretofore been utilized. The medium avoids the early death of cells as compared with previous culture mediums that have been used. The pituitary cells are able to incorporate radioactive labeled thymidine which is an evidence of cell growth and proliferation. The medium also prevents the growth or formation of fibroblasts or the conversion of the anterior pituitary growth hormone cells into a fibroblastic type cell. Fibroblastic transformation is a common problem with presently available tissue culture systems. The medium permits cell growth and multiplication as is evident by mitotic activity within the cells, and a two to four-fold growth about every 8 days of cells which continue to be capable of continuing production of growth hormone. This has been repeatedly confirmed by radioimmune assay for human growth hormone at every sub-culture done to increase the number of flasks with cells producing growth hormone. We have found that human growth hormone undergoes a degradation of 50% every three days in the medium used for their growth and proliferation. In spite of such a concommitant degradation, we have been able to obtain large amounts of human growth hormone by this new culture technique utilizing our new media.

There is a great need to produce human anterior pituitary growth hormone as it is, at present, in high demand. At present human growth hormone is prepared by a process of direct extraction of growth hormone from fresh pituitary glands obtained from humans at autopsy. The amount of human growth hormone that can be produced by this method is very small. The supply now available is but a fraction of the amount needed to treat human infants and children with growth hormone deficiencies. Previously pituitary growth hormones were extracted from animal pituitary glands (sheep, beef, pig and even fish) and were used to treat human subjects. Treatment trials about 20 years ago with these hormones resulted in failure because animal growth hormones were a foreign type of protein which produced neutralizing antibodies in the patients, rendering the animal growth hormone ineffective. It is now known that only the molecular species of human growth hormone obtained from human pituitaries can be used in human subjects.

The distinct advantages of the medium, when used in an appropriate culture procedure, are as follows: One whole human pituitary gland provides about 2 to 3 milligrams of extractable human growth hormone. Utilizing the above medium and starting with a small single inoculum of about two-thirds of a human anterior pituitary gland which contains approximately 2 milligrams of extractable growth hormone, as the initial cell culture inoculum, one achieves 10 milligrams available in the media within 8 days, approximately 20 milligrams by 16 days, approximately 40 milligrams by 24 days, and so on, utilizing a serial dilution sub-culture procedure and the herein-defined nutrient media. Hence, the initial inoculum of pituitary cells provides an amount of growth hormone available in the medium for extraction and purification that is approximately 20 times more than that present in the initial pituitary tissue which was used as the seed culture in a period of 24 days. Since there is a concommitant degradation of 50% of the growth hormone in the media every three days, these values represent human growth hormone produced above and beyond that degraded concommitantly.

The process of the present invention is adaptable to continuous fermentation. Modifications of our present harvesting system by the use of appropriate filters to collect only the media at shorter intervals than 4 to 8 days, followed by recycling of the media after extraction of the secreted growth hormone by a continuous fermentation process would enable one to produce larger amounts of growth hormone.

Our experiments have confirmed that the growth hormone extracted and purified from our process of tissue culture is biologically active, using the presently available bioassays. It has 2 units bioactivity=1 mg immunoreactivity which is the optimum bioactivity seen with human growth hormones available at present. Another advantage of a tissue culture procedure for production of human growth hormone is that at least 80 to 90% of the human growth hormone is in the monomer form, the simple physiologically active form. Direct extraction of growth hormones from human pituitary glands provides, in addition to monomer, dimers and polymers; the two latter are thought to be antigenic in human subjects. Most human growth hormones available today contain monomers, dimers, polymers (approximately one-third each), the growth hormone from the Scandinavian agencies (NIL-Denmark, KABI-Sweden), being better in terms of a purer monomer content than the growth hormone made by the U.S. National Pituitary Agency. It is interesting to note that the growth hormone made by our process, because of its almost pure monomeric content, is far superior to those currently available.

At present the cost of treatment of one child with a growth hormone deficiency is very high. Such treatment must be maintained throughout the entire growing span for the child. Preliminary studies by the inventors indicate that the growth hormone can be extracted from the medium utilizing minor modifications of the extraction procedures now used for direct extraction of growth hormone from fresh gland tissues. It is estimated that the cost of preparation and extraction will not be greatly different than the processes now utilized. However, the distinct advantage resides in the ability to obtain as much as 20 times more growth hormone in about three weeks time than can be obtained by extraction of one pituitary gland.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A nutrient culture medium composition adapted to the production of growth hormone from pituitary cells by serial subculturing, said composition consisting essentially of effective amounts of an amino acid-rich nutrient medium supplemented by the addition of minor amounts of liver extract, insulin, and anti-biotic and anti-fungal agents.

2. A composition according to claim 1 further characterized in that the amino acid-rich medium is Medium 199-1X with Earle's modified salts.

3. A composition according to claim 2 further characterized in that said medium composition includes about 5 to 20 ml of liver extract and about 6 to 20 I.U. of insulin per liter of Medium 199-1X.

4. A composition according to claim 1 further characterized in that said medium composition consists essentially of Medium 199-1X with Earle's modified salts supplemented by about 10 ml injectable liver extract containing B vitamins, about 10 I.U. crystalline insulin, about 500,000 units crystalline sodium penicillin G, about 500 mg streptomycin sulfate and about 50,000 units of nystatin per liter.

5. A process for the production of growth hormone which comprises:

(A) preparing a nutrient amino acid-rich medium composition according to claim 1 in an open aeration incubation vessel, (B) dispersing cells of the anterior pituitary in said medium, (C) initially maintaining said cells under aerated cell growth conditions for several days, (D) sub-culturing the resulting initial culture and reconstituting the original volume with additional medium, (E) maintaining the sub-cultures under aerated cell growth conditions for an additional several days, (F) serially sub-culturing every several days until the desired optimum growth level is reached, and (G) separating the [media] *medium* from the cells and extracting *from the medium* the growth hormone from the sub-culture cells.

6. A process according to claim 5 further characterized in that said pituitary is human and said hormone is human growth hormone.

7. A process according to claim 5 further characterized in that the amino acid-rich medium is Medium 199-1X with Earle's modified salts.

8. A process according to claim 7 further characterized in that said medium composition includes about 5 to 20 ml of liver extract and about 6 to 20 I.U. of insulin per liter of Medium 199-1X.

9. A process according to claim 6 further characterized in that said medium composition consists essentially of Medium 199-1X with Earle's modified salts supplemented by about 10 ml injectable liver extract containing B vitamins, about 10 I.U. crystalline insulin, about 500,000 units crystalline sodium penicillin G, about 500 mg streptomycin sulfate and about 50,000 units of nystatin per liter.

10. A process according to claim 6 further characterized in that said initial culture is incubated for about 8 days.

11. A process according to claim 6 further characterized in that said sub-cultures are incubated for about 4 to 8 days.

12. A process according to claim 6 further characterized in that said initial culture is sub-cultured at least 4 times to obtain optimal growth level.

13. A process according to claim 6 further characterized in that said cultures are aerated by a positive flow of sterile air without added carbon dioxide.

* * * * *